United States Patent
Soya

(10) Patent No.: US 9,176,066 B2
(45) Date of Patent: Nov. 3, 2015

(54) METHOD FOR PRESERVING AQUEOUS SOLUTION CONTAINING LEUCO CHROMOGEN

(75) Inventor: Haruyo Soya, Shizuoka (JP)

(73) Assignee: KYOWA MEDEX CO., LTD., Tokyo (JP)

(*) Notice: Subject to any disclaimer, the term of this patent is extended or adjusted under 35 U.S.C. 154(b) by 276 days.

(21) Appl. No.: 13/991,655

(22) PCT Filed: Dec. 12, 2011

(86) PCT No.: PCT/JP2011/078670
§ 371 (c)(1),
(2), (4) Date: Jun. 5, 2013

(87) PCT Pub. No.: WO2012/081540
PCT Pub. Date: Jun. 21, 2012

(65) Prior Publication Data
US 2013/0252343 A1 Sep. 26, 2013

(30) Foreign Application Priority Data
Dec. 13, 2010 (JP) .................. 2010-276551

(51) Int. Cl.
| | |
|---|---|
| *G01N 21/00* | (2006.01) |
| *G01N 21/78* | (2006.01) |
| *C07D 279/30* | (2006.01) |
| *C09B 57/10* | (2006.01) |
| *C09B 67/22* | (2006.01) |
| *C09B 67/44* | (2006.01) |
| *C09B 67/30* | (2006.01) |
| *C07D 213/72* | (2006.01) |

(52) U.S. Cl.
CPC .............. *G01N 21/78* (2013.01); *C07D 213/72* (2013.01); *C07D 279/30* (2013.01); *C09B 57/10* (2013.01); *C09B 67/0033* (2013.01); *C09B 67/0078* (2013.01); *C09B 67/0083* (2013.01)

(58) Field of Classification Search
None
See application file for complete search history.

(56) References Cited

U.S. PATENT DOCUMENTS

| | | |
|---|---|---|
| 2003/0203495 A1 | 10/2003 | Rupp |
| 2008/0241816 A1 | 10/2008 | Taniguchi et al. |
| 2011/0015391 A1 | 1/2011 | Yonehara et al. |

FOREIGN PATENT DOCUMENTS

| | | |
|---|---|---|
| JP | 57-029297 | 2/1982 |
| JP | 62-093261 | 4/1987 |
| JP | 03-206896 | 9/1991 |
| JP | 2005-110507 | 4/2005 |
| JP | 2005-524071 | 8/2005 |
| JP | 2010-189662 | 9/2010 |
| WO | 03/091725 | 11/2003 |
| WO | 2005/088305 | 9/2005 |
| WO | 2007/083703 | 7/2007 |
| WO | 2009/116575 | 9/2009 |

OTHER PUBLICATIONS

Aoyama, "H2O2-POD group", Clinical Testing, vol. 41, No. 9 (1997) 1014-19.

*Primary Examiner* — Robert Xu
(74) *Attorney, Agent, or Firm* — Fitzpatrick, Cella, Harper & Scinto

(57) ABSTRACT

The present invention provides: a method for preserving an aqueous solution containing a leuco chromogen, comprising adding a compound having at least one substituent selected from the group consisting of a nitroso group and an azo group and having an ability to coordinate a metal ion or a salt thereof to the aqueous solution containing a leuco chromogen; a method for stabilizing a leuco chromogen, comprising allowing the leuco chromogen to coexist in an aqueous solution comprising a compound having at least one substituent selected from the group consisting of a nitroso group and an azo group and having an ability to coordinate a metal ion or a salt thereof; and a liquid reagent comprising a leuco chromogen and a compound having at least one substituent selected from the group consisting of a nitroso group and an azo group and having an ability to coordinate a metal ion or a salt thereof.

6 Claims, No Drawings

METHOD FOR PRESERVING AQUEOUS SOLUTION CONTAINING LEUCO CHROMOGEN

This application is a National Phase of PCT Application No. PCT/JP2011/078670 filed Dec. 12, 2011, which turn claims benefit of Japanese Application No. 2010-276551 filed Dec. 13, 2010.

TECHNICAL FIELD

The present invention relates to a method for preserving an aqueous solution containing a leuco chromogen, a method for stabilizing a leuco chromogen, and a liquid reagent comprising a leuco chromogen.

BACKGROUND ART

A leuco chromogen is a chromogen that generates a dye through reaction with hydrogen peroxide in the presence of a peroxidative substance such as peroxidase. Unlike a coupling-type chromogen, the leuco chromogen generates a dye by itself. For example, phenothiazine leuco chromogens, triphenylmethane leuco chromogens, and diphenylamine leuco chromogens are known (see e.g., patent documents 1 to 3).

The leuco chromogen is often used, as in the coupling-type chromogen, in the quantification of an analyte component such as cholesterol and glycated hemoglobin contained in a sample such as serum. Specifically, clinical laboratory examinations often involve: converting an analyte component in a sample into hydrogen peroxide; reacting the generated hydrogen peroxide with a leuco chromogen in the presence of a peroxidative substance such as peroxidase to convert the chromogen to a dye; and quantifying the analyte component in the sample on the basis of the absorbance of the generated dye. Particularly, the leuco chromogen is preferably used as a highly sensitive chromogen in the quantification of an analyte component contained only in a trace amount in a sample (see e.g., non-patent document 1).

Thus, the leuco chromogen is used as a highly sensitive chromogen in the quantification of a trace amount of an analyte component in a sample, while the leuco chromogen has poor storage stability and undesirably develops color spontaneously with time, particularly in a solution. To solve this problem of poor stability of the leuco chromogen, methods for stabilizing the leuco chromogen in a solution have been studied and reported so far (see e.g., patent documents 4 and 5). These methods for stabilizing the leuco chromogen, however, are not always satisfactory, for example, because they must be performed under strict conditions.

PRIOR ART DOCUMENTS

Patent Documents

Patent Document 1: Japanese unexamined Patent Application Publication No. 57-029297
Patent Document 2: Japanese unexamined Patent Application Publication No. 3-206896
Patent Document 3: Japanese unexamined Patent Application Publication No. 62-093261
Patent Document 4: WO2005/088305
Patent Document 5: WO2007/083703

Non-Patent Document

Non-patent Document 1: Journal of Medical Technology, 1997, Vol. 41, No. 9, pp. 1014-1019

SUMMARY OF THE INVENTION

Problems to be Solved by the Invention

An object of the present invention is to provide a method for preserving an aqueous solution containing a leuco chromogen, and a method for stabilizing a leuco chromogen, whereby the leuco chromogen is stably preserved in an aqueous solution, and to provide a reagent for stably preserving a leuco chromogen.

Means to Solve the Problems

The present inventors have conducted diligent studies to solve the problems and consequently found that a leuco chromogen is stably preserved by adding a compound having at least one substituent selected from the group consisting of a nitroso group and an azo group and having an ability to coordinate a metal ion or a salt thereof to an aqueous solution containing a leuco chromogen. On the basis of the findings, the present invention has been completed. Specifically, the present invention relates to the following [1] to [9]:

[1] A method for preserving an aqueous solution containing a leuco chromogen, comprising adding a compound having at least one substituent selected from the group consisting of a nitroso group and an azo group and having an ability to coordinate a metal ion or a salt thereof to the aqueous solution containing a leuco chromogen.

[2] A method for stabilizing a leuco chromogen, comprising allowing the leuco chromogen to coexist in an aqueous solution comprising a compound having at least one substituent selected from the group consisting of a nitroso group and an azo group and having an ability to coordinate a metal ion or a salt thereof.

The method according to [1] or [2], wherein the compound having at least one substituent selected from the group consisting of a nitroso group and an azo group and having an ability to coordinate a metal ion, or the salt thereof is a compound represented by the following general formula (I) or a salt thereof:

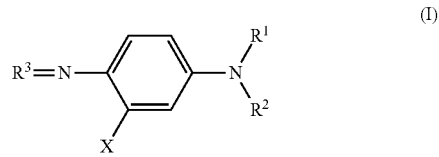

(wherein $R^1$ and $R^2$ are the same or different and each represent a hydrogen atom or a substituted or unsubstituted alkyl group; $R^3$ represents an oxygen atom or a group represented by $R^4$—N (in which $R^4$ represents a substituted or unsubstituted 2-pyridyl) and X represents a hydroxy group or an amino group).

[4] The method according to any one of [1] to [3], wherein the leuco chromogen is a phenothiazine chromogen.

[5] The method according to [4], wherein the phenothiazine chromogen is 10-(carboxymethylaminocarbonyl)-3,7-bis(dimethylamino)phenothiazine.

[6] A liquid reagent comprising a leuco chromogen and a compound having at least one substituent selected from the group consisting of a nitroso group and an azo group and having an ability to coordinate a metal ion or a salt thereof.

[7] The reagent according to [6], wherein the compound having at least one substituent selected from the group consisting of a nitroso group and an azo group and having an ability to coordinate a metal ion, or the salt thereof is a compound represented by the following general formula (I) or a salt thereof:

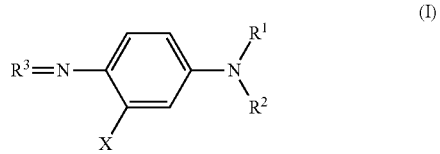

(wherein $R^1$ and $R^2$ are the same or different and each represent a hydrogen atom or a substituted or unsubstituted alkyl group; $R^3$ represents an oxygen atom or a group represented by $R^4$—N (in which $R^4$ represents a substituted or unsubstituted 2-pyridyl) and X represents a hydroxy group or an amino group).

[8] The reagent according to [6] or [7], wherein the leuco chromogen is a phenothiazine chromogen.

[9] The reagent according to [8], wherein the phenothiazine chromogen is 10-carboxymethylaminocarbonyl)-3,7-bis(dimethylamino)phenothiazine.

Effect of the Invention

The present invention provides a method for preserving an aqueous solution containing a leuco chromogen, a method for stabilizing a leuco chromogen, and a liquid reagent comprising a leuco chromogen, whereby the leuco chromogen is stably preserved in an aqueous solution. The methods and the reagent of the present invention are useful in, for example, the measurement of glycated hemoglobin that is used in the diagnosis of diabetes mellitus.

Mode of Carrying Out the Invention (1) Method for Preserving an Aqueous Solution Containing a Leuco Chromogen and Method for Stabilizing a Leuco Chromogen The present invention relates to a method for preserving an aqueous solution containing a leuco chromogen. According to the method for preserving an aqueous solution containing a leuco chromogen of the present invention, the leuco chromogen can be stably preserved in an aqueous solution. The phrase "a leuco chromogen is stably preserved in an aqueous solution" means that the leuco chromogen in the aqueous solution is not only stable against heat but also stable against light.

The method for preserving an aqueous solution containing a leuco chromogen according to the present invention comprises adding a compound having at least one substituent selected from the group consisting of a nitroso group and an azo group and having an ability to coordinate a metal ion or a salt thereof to the aqueous solution containing a leuco chromogen.

In the present invention, the compound having at least one substituent selected from the group consisting of a nitroso group and an azo group and having an ability to coordinate a metal ion, or the salt thereof is not particularly limited as long as the compound or the salt thereof has at least one substituent selected from the group consisting of a nitroso group and an azo group, has an ability to coordinate a metal ion, and is capable of stably preserving the leuco chromogen. Examples thereof include a compound represented by the following general formula (I) or a salt thereof [hereinafter, referred to as compound (I)]:

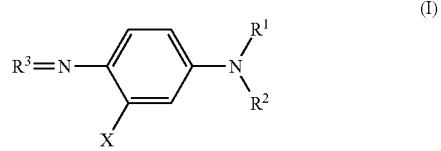

(wherein $R^1$ and $R^2$ are the same or different and each represent a hydrogen atom or a substituted or unsubstituted alkyl group; $R^3$ represents an oxygen atom or a group represented by $R^4$—N; $R^4$ represents substituted or unsubstituted 2-pyridyl; and X represents a hydroxy group or an amino group).

Examples of the alkyl group in the compound (I) include alkyl groups having 1 to 6 carbon atoms, such as a methyl group, an ethyl group, a propyl group, a butyl group, a pentyl group, and a hexyl group. Examples of the substituent in the substituted alkyl group include a sulfo group, a carboxyl group, a hydroxy group, an amido group, and a halogen atom. Examples of the halogen atom include a chlorine atom, a bromine atom, and an iodine atom. Examples of the substituent in the substituted 2-pyridyl include an electron-donating group and an electron-withdrawing group, and an electron-withdrawing group is preferred.

Examples of the electron-donating group include an alkyl group, an alkoxy group, a hydroxy group, a substituted or unsubstituted amino group, and a thioalkyl group. Examples of alkyl in the alkyl group and the alkoxy group include alkyl having 1 to 6 carbon atoms, such as methyl, ethyl, propyl, butyl, pentyl, and hexyl. Examples of the substituted amino group include an N-monosubstituted amino group and N,N-disubstituted amino group. Examples of the substituent in the substituted amino group include the alkyl group described above.

Examples of the electron-withdrawing group include a nitro group, a cyano group, a formyl group, an acyl group, a halogen atom, a sulfo group, and a carboxyl group. Specific examples of the substituted 2-pyridyl include 5-nitro-2-pyridyl, 5-chloro-2-pyridyl, 5-bromo-2-pyridyl, 5-iodo-2-pyridyl, 5-sulfo-2-pyridyl, and 5-carboxy-2-pyridyl. Examples of the salt include a lithium salt, a sodium salt, a potassium salt, an ammonium salt, and a calcium salt. Also, the compound (I) includes a hydrate.

Specific examples (products) of the compound (I) include Nitroso-PSAP {2-nitroso-5-[N-propyl-N-(3-sulfopropyl)amino]phenol}, Nitro-PAPS {2-(5-nitro-2-pyridylazo)-5-[N-propyl-N-sulfopropyl)amino]phenol disodium salt dihydrate}, 5-Br-PSAA {2-(5-bromo-2-pyridylazo)-5-[N-propyl-N-(sulfopropyl)amino]aniline sodium salt}, and 5-Br-PAPS {2-(5-bromo-2-pyridylazo)-5-[N-propyl-N-(sulfopropyl)amino]phenol disodium salt dihydrate} (all manufactured by Dojindo Laboratories).

In the method for preserving a leuco chromogen according to the present invention, the preservation stability of the leuco chromogen can be evaluated on the basis of the coloring of the aqueous solution containing a leuco chromogen. It can be evaluated that the stronger the coloring, i.e., the larger the absorbance of the aqueous solution containing a leuco chromogen, the poorer the stability of leuco chromogen. By contrast, it can be evaluated that the weaker the coloring, i.e., the smaller the absorbance of the aqueous solution containing a leuco chromogen, the better the stability of leuco chromogen.

The aqueous solution containing a leuco chromogen according to the present invention is an aqueous solution containing a leuco chromogen dissolved in an aqueous medium and can be prepared by addition of the leuco chromogen to the aqueous medium and dissolution. The aqueous medium in which the leuco chromogen is dissolved is not particularly limited as long as the leuco chromogen is dissolved therein. Examples thereof include a deionized water, a distilled water, or a buffer solution. A buffer solution is preferred. For the preparation of the aqueous solution containing a leuco chromogen, an organic solvent can be used as a solubilizer for the dissolution of the leuco chromogen in the aqueous medium. The leuco chromogen dissolved in the organic solvent can be added to the aqueous medium and dissolved in the aqueous medium to prepare the aqueous solution containing a leuco chromogen. The organic solvent is not particularly limited as long as the leuco chromogen is dissolved therein. Examples thereof include dimethylformamide (DMF), dimethyl sulfoxide (DMSO), dioxane, acetone, methanol, and ethanol.

The pH of the aqueous medium is not particularly limited as long as the leuco chromogen is dissolved. The pH is, for example, 4 to 10. In the case of using a buffer solution as the aqueous medium, a buffer is preferably used according to the set pH. Examples of the buffer used in the buffer solution include a tris(hydroxymethyl)aminomethane buffer, a phosphate buffer, a borate buffer, and a Good's buffer.

Examples of the Good's buffer include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

The concentration of the buffer solution is not particularly limited as long as the leuco chromogen is dissolved. The concentration is usually 0.001 to 2.0 mol/L, preferably 0.005 to 1.0 mol/L.

Examples of the leuco chromogen according to the present invention include a phenothiazine chromogen, a triphenylmethane chromogen, a diphenylamine chromogen, o-phenylenediamine, hydroxypropionic acid, diaminobenzidine, and tetramethylbenzidine. A phenothiazine chromogen is preferred. Examples of the phenothiazine chromogen include 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), and 10-N-(carboxymethylaminocarbonyl)-3,7-bis(dimethylamino)-10H-phenothiazine sodium salt (DA-67). Among these phenothiazine chromogens, 10-N-(carboxymethylaminocarbonyl)-3,7-bis(dimethylamino)-10H-phenothiazine sodium salt (DA-67) is particularly preferred. Examples of the triphenylmethane chromogen include N,N,N',N',N'',N''-hexa(3-sulfopropyl)-4,4',4''-triaminotriphenylmethane (TPM-PS). Examples of the diphenylamine chromogen include N-(carboxymethylaminocarbonyl)-4,4'-bis(dimethylamino)diphenylamine sodium salt (DA-64), 4,4'-bis(dimethylamino)diphenylamine, and bis[3-bis(4-chlorophenyl)methyl-4-dimethylaminophenyl]amine (BCMA).

The present invention further relates to a method for stabilizing a leuco chromogen. The stabilization of the leuco chromogen according to the present invention means that the leuco chromogen in an aqueous solution containing a leuco chromogen is not only stabilized against heat but also stabilized against light. In this context, the stabilization of the leuco chromogen can be evaluated on the basis of the coloring of the aqueous solution containing the leuco chromogen. It can be evaluated that the stronger the coloring, i.e., the larger the absorbance of the aqueous solution containing a leuco chromogen, the poorer the stability of leuco chromogen. By contrast, it can be evaluated that the weaker the coloring, i.e., the smaller the absorbance of the aqueous solution containing a leuco chromogen, the better the stability of leuco chromogen.

The method for stabilizing a leuco chromogen according to the present invention comprises allowing the leuco chromogen to coexist in an aqueous solution comprising a compound having at least one substituent selected from the group consisting of a nitroso group and an azo group and having an ability to coordinate a metal ion or a salt thereof. Examples of the compound having at least one substituent selected from the group consisting of a nitroso group and an azo group and having an ability to coordinate a metal ion, or the salt thereof used in the method for stabilizing a leuco chromogen according to the present invention include the compound having at least one substituent selected from the group consisting of a nitroso group and an azo group and having an ability to coordinate a metal ion, or the salt thereof as described above, and specifically include compound (I).

Examples of the leuco chromogen and the aqueous solution containing a leuco chromogen used in the stabilization method of the present invention include the leuco chromogen and the aqueous solution containing a leuco chromogen as described in the method for preserving a leuco chromogen. In the present invention, the concentration of the leuco chromogen in the aqueous solution containing a leuco chromogen is not particularly limited as long as the leuco chromogen is dissolved in the aqueous medium. The concentration is usually 0.0001 to 2.0 mmol/L, preferably 0.0005 to 1.0 mmol/L.

In the present invention, the concentration of the compound having at least one substituent selected from the group consisting of a nitroso group and an azo group and having an ability to coordinate a metal ion, or the salt thereof, which coexists with the leuco chromogen in the aqueous solution is usually 0.0001 to 200 μmol/L, preferably 0.005 to 100 μmol/L.

A method for determining the stability of the leuco chromogen against heat according to the present invention is not particularly limited as long as the method can determine the stability of the leuco chromogen against heat. Examples thereof include a method which involves storing an aqueous solution containing a leuco chromogen at 5° C. or 30° C. and then determining the coloring of the aqueous solution containing a leuco chromogen using an absorption spectrometer.

Likewise, a method for determining the stability of the leuco chromogen against light according to the present invention is not particularly limited as long as the method can determine the stability of the leuco chromogen against light. Examples thereof include a method which involves irradiating an aqueous solution containing a leuco chromogen with light for 15 hours and then determining the coloring of the aqueous solution containing a leuco chromogen using an absorption spectrometer.

(2) Liquid Reagent

The liquid reagent of the present invention is a liquid reagent comprising a leuco chromogen and a compound having at least one substituent selected from the group consisting of a nitroso group and an azo group and having an ability to coordinate a metal ion or a salt thereof.

In the liquid reagent of the present invention, the leuco chromogen coexists, in an aqueous medium, with the compound having at least one substituent selected from the group consisting of a nitroso group and an azo group and having an ability to coordinate a metal ion, or the salt thereof. Examples of the leuco chromogen in the liquid reagent of the present invention include the aforementioned leuco chromogen. Examples of the aqueous medium in the liquid reagent of the present invention include the aforementioned aqueous medium. Examples of the compound having at least one substituent selected from the group consisting of a nitroso group and an azo group and having an ability to coordinate a metal ion, or the salt thereof in the liquid reagent of the present invention include the aforementioned compound having at least one substituent selected from the group consisting of a nitroso group and an azo group and having an ability to coordinate a metal ion, or the salt thereof, and specifically include compound (I).

A concentration of the compound having at least one substituent selected from the group consisting of a nitroso group and an azo group and having an ability to coordinate a metal ion, or the salt thereof in the liquid reagent of the present invention is usually 0.0001 to 10%, preferably 0.0005 to 5%. A concentration of the leuco chromogen in the liquid reagent of the present invention is not particularly limited as long as the leuco chromogen is dissolved in the aqueous medium, and is usually 0.0001 to 2.0 mmol/L, preferably 0.0005 to 1.0 mmol/L. The aforementioned organic solvent can be used as a solubilizer for the dissolution of the leuco chromogen in the aqueous medium.

Hereinafter, the present invention will be described more specifically with reference to Examples. However, these Examples do not limit the scope of the present invention by any means.

Reagents and enzymes from the following manufacturers were used in these Examples, Comparative Examples, and Test Examples.

MES (manufactured by Dojindo Laboratories), peroxidase (manufactured by Toyobo Co., Ltd.), BSA (manufactured by Proliant Inc.), Nitroso-PSAP [compound (I); manufactured by Dojindo Laboratories], and 5-Br-PSAA [compound (I); manufactured by Dojindo Laboratories].

Example 1

A DA-67-containing aqueous solution having the following composition was prepared:

| MES (pH 6.3) | 10 mmol/L |
| DA-67 | 20 μmol/L |
| Nitroso-PSAP | 1 μmol/L |

Example 2

A DA-67-containing aqueous solution having the following composition was prepared:

| MES (pH 6.3) | 10 mmol/L |
| DA-67 | 20 μmol/L |
| 5-Br-PSAA | 5 μmol/L |

[Comparative Example 1]

A DA-67-containing aqueous solution having the following composition was prepared:

| MES (pH 6.3) | 10 mmol/L |
| DA-67 | 20 μmol/L |

Example 3

(1) Preparation of Sample for DA-67 Stability Assay

The DA-67-containing aqueous solution of Example 1 was stored at 5° C. for 7 days or at 30° C. for 7 days. The resulting solutions were used as samples for DA-67 stability assay.

(2) Preparation of Reagent for Stability Assay

A reagent for stability assay having the following composition was prepared:

<Reagent for DA-67 Stability Assay>

| MES (pH 6.3) | 10 mmol/L |
| BSA | 0.005% |

(3) Evaluation of Stability of DA-67 in DA-67-Containing Aqueous Solution

120 μL of the reagent for DA-67 stability assay prepared in the paragraph (2) was added to 30 μL of the freshly prepared DA-67-containing aqueous solution of Example 1, and the mixture was heated at 37° C. for 5 minutes. Then, the absorbance ($E_{freshly\ prepared}$) Of the solution was measured at a main wavelength of 660 nm and a sub wavelength of 800 nm using Hitachi 7170S. The same assay as described above was performed using the reagent for DA-67 stability assay of the paragraph (2) instead of the freshly prepared DA-67-containing aqueous solution to determine absorbance ($E_{blank}$). $E_{blank}$ was subtracted from $E_{freshly\ prepared}$ to determine absorbance ($\Delta E_{freshly\ prepared}$) for the freshly prepared DA-67-containing aqueous solution.

Similarly, the DA-67-containing aqueous solution stored at 5° C. for 7 days and the DA-67-containing aqueous solution stored at 30° C. for 7 days were used as samples in measurement to determine absorbance ($\Delta E_{5°\ C.}$) for the DA-67-containing aqueous solution stored at 5° C. for 7 days and absorbance ($\Delta E_{30°\ C.}$) for the DA-67-containing aqueous solution stored at 30° C. for 7 days.

$\Delta E_{freshly\ prepared}$ was subtracted from each of the $\Delta E_{5°\ C.}$ and $\Delta E_{30°\ C.}$ thus determined, and the determined values were designated as $\Delta E_1$ and $\Delta E_2$, respectively, which were used as indexes for the stability of DA-67. The results are shown in Table 1. Both the values of $\Delta E_1$ and $\Delta E_2$ closer to 0 represent that the aqueous solution is prevented from being colored and DA-67 is stably preserved in the aqueous solution, i.e., DA-67 is stabilized in the aqueous solution.

Example 4

$\Delta E_1$ and $\Delta E_2$ were determined in the same way as in Example 3 except that the DA-67-containing aqueous solution of Example 2 was used instead of the DA-67-containing aqueous solution of Example 1. The results are shown in Table 1.

[Comparative Example 2]

ΔE₁ and ΔE₂ were determined in the same way as in Example 3 except that the DA-67-containing aqueous solution of Comparative Example 1 was used instead of the DA-67-containing aqueous solution of Example 1. The results are shown in Table 1.

TABLE 1

|  | Compound (I) |  | Change in absorbance after 7-day storage ||
|---|---|---|---|---|
|  |  |  | $\Delta E_1$ (Stored at 5° C.) | $\Delta E_2$ (Stored at 30° C.) |
| Comparative Example 2 | — |  | 0.003 | 0.067 |
| Example 3 | Nitroso-PSAP | 1 μmol/L | 0.002 | 0.029 |
| Example 4 | 5-Br-PSAA | 5 μmol/L | 0.002 | 0.036 |

As shown in Table 1, in the comparison of Examples 3 and 4 with Comparative Example 2, the aqueous solution containing Nitroso-PSAP or 5-Br-PSAA as the compound (I) was more significantly prevented from being colored after storage both at 5° C. and at 30° C. than the aqueous solution free from the compound (I). Since the compound (I) is a compound having at least one substituent selected from the group consisting of a nitroso group and an azo group and having an ability to coordinate a metal ion, or a salt thereof, it proved that: DA-67 in the aqueous solution containing the compound having at least one substituent selected from the group consisting of a nitroso group and an azo group and having an ability to coordinate a metal ion, or the salt thereof is stable against heat; the DA-67-containing aqueous solution is stably preserved by the compound having at least one substituent selected from the group consisting of a nitroso group and an azo group and having an ability to coordinate a metal ion, or the salt thereof; and DA-67 is stabilized in the aqueous solution by the compound having at least one substituent selected from the group consisting of a nitroso group and an azo group and having an ability to coordinate a metal ion, or the salt thereof.

Example 5

A DA-67-containing aqueous solution having the following composition was prepared:

| MES (pH 6.3) | 10 mmol/L |
|---|---|
| DA-67 | 20 μmol/L |
| Nitroso-PSAP | 5 μmol/L |

Example 6

A DA-67-containing aqueous solution having the following composition was prepared:

| MES (pH 6.3) | 10 mmol/L |
|---|---|
| DA-67 | 20 μmol/L |
| Nitroso-PSAP | 10 μmol/L |

Example 7

A DA-67-containing aqueous solution having the following composition was prepared:

| MES (pH 6.3) | 10 mmol/L |
|---|---|
| DA-67 | 20 μmol/L |
| 5-Br-PSAA | 10 μmol/L |

Example 8

(1) Preparation of Sample for DA-67 Stability Assay

The DA-67-containing aqueous solution of Example 5 irradiated with 1100-lux light for 24 hours was used as a sample for DA-67 stability assay.

(2) Preparation of Reagent for Stability Assay

A reagent for stability assay having the following composition was prepared:

<Reagent for DA-67 Stability Assay>

| MES (pH 6.3) | 10 mmol/L |
|---|---|
| BSA | 0.005% |

(3) Evaluation of stability of DA-67 against light

120 μL of the reagent for DA-67 stability assay prepared in the paragraph (2) was added to 30 μL of the freshly prepared DA-67-containing aqueous solution of Example 5, and the mixture was heated at 37° C. for 5 minutes. Then, the absorbance ($E_{freshly\,prepared}$) of the solution was measured at a main wavelength of 660 nm and a sub wavelength of 800 nm using Hitachi 7170S. The same assay as described above was performed using the reagent for DA-67 stability assay of the paragraph (2) instead of the freshly prepared DA-67-containing aqueous solution to determine absorbance ($E_{blank}$). $E_{blank}$ was subtracted from $E_{freshly\,prepared}$ to determine absorbance ($\Delta E_{freshly\,prepared}$) for the freshly prepared DA-67-containing aqueous solution.

Similarly, the light-irradiated DA-67-containing aqueous solution prepared in the paragraph (1) was used as a sample in measurement to determine absorbance ($\Delta E_{light}$) for the light-irradiated DA-67-containing aqueous solution.

$\Delta E_{freshly\,prepared}$ was subtracted from the $\Delta E_{light}$ thus determined, and the determined value was designated as $\Delta E_3$, which was used as an index for the stability of DA-67 against light. The results are shown in Table 2. The value of $\Delta E_3$ closer to 0 represents that DA-67 is prevented from being colored due to light irradiation.

Example 9

$\Delta E_3$ was determined in the same way as in Example 8 except that the DA-67-containing aqueous solution of Example 6 was used instead of the DA-67-containing aqueous solution of Example 5. The results are shown in Table 2.

Example 10

$\Delta E_3$ was determined in the same way as in Example 8 except that the DA-67-containing aqueous solution of Example 2 was used instead of the DA-67-containing aqueous solution of Example 5. The results are shown in Table 2.

Example 11

$\Delta E_3$ was determined in the same way as in Example 8 except that the DA-67-containing aqueous solution of Example 7 was used instead of the DA-67-containing aqueous solution of Example 5. The results are shown in Table 2.

[Comparative Example 3]

$\Delta E_3$ was determined in the same way as in Example 8 except that the DA-67-containing aqueous solution of Comparative Example 1 was used instead of the DA-67-containing aqueous solution of Example 5. The results are shown in Table 2.

TABLE 2

| | Compound (I) | | ΔE₃ (Change in absorbance after 24-hour light irradiation) |
|---|---|---|---|
| Comparative Example 3 | — | | 0.064 |
| Example 8 | Nitroso-PSAP | 5 μmol/L | 0.011 |
| Example 9 | Nitroso-PSAP | 10 μmol/L | 0.001 |
| Example 10 | 5-Br-PSAA | 5 μmol/L | 0.023 |
| Example 11 | 5-Br-PSAA | 10 μmol/L | 0.013 |

As shown in Table 2, in the comparison of Examples 8 to 11 with Comparative Example 3, the aqueous solution containing Nitroso-PSAP or 5-Br-PSAA as the compound (I) was more significantly prevented from being colored due to light irradiation than the aqueous solution free from the compound (I). Since the compound (I) is a compound having at least one substituent selected from the group consisting of a nitroso group and an azo group and having an ability to coordinate a metal ion, or a salt thereof, it proved that: DA-67 in the aqueous solution containing the compound having at least one substituent selected from the group consisting of a nitroso group and an azo group and having an ability to coordinate a metal ion, or the salt thereof is stable against light; the DA-67-containing aqueous solution is stably preserved by the compound having at least one substituent selected from the group consisting of a nitroso group and an azo group and having an ability to coordinate a metal ion, or the salt thereof; and DA-67 is stabilized by the compound having at least one substituent selected from the group consisting of a nitroso group and an azo group and having an ability to coordinate a metal ion, or the salt thereof.

INDUSTRIAL APPLICABILITY

The present invention provides a method for preserving an aqueous solution containing a leuco chromogen, a method for stabilizing a leuco chromogen, and a liquid reagent comprising a leuco chromogen. The methods and the reagent of the present invention are useful in, for example, the measurement of glycated hemoglobin used in the diagnosis of diabetes mellitus.

The invention claimed is:

1. A method for preserving an aqueous solution containing a leuco chromogen, comprising the steps of adding to the aqueous solution containing said leuco chromogen a compound having at least one substituent selected from the group consisting of a nitroso group and an azo group and having an ability to coordinate a metal ion or a salt thereof, wherein
the compound having at least one substituent selected from the group consisting of a nitroso group and an azo group and having an ability to coordinate a metal ion, or the salt thereof is a compound represented by the following general formula (I) or a salt thereof:

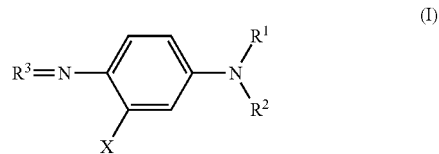

(wherein $R^1$ and $R^2$ are the same or different and each represent a hydrogen atom or a substituted or unsubstituted alkyl group; $R^3$ represents an oxygen atom or a group represented by $R^4$—N (in which $R^4$ represents a substituted or unsubstituted 2-pyridyl) and X represents a hydroxy group or an amino group).

2. The method according to claim 1, wherein the leuco chromogen is a phenothiazine chromogen.

3. The method according to claim 2, wherein the phenothiazine chromogen is 10-(carboxymethylaminocarbonyl)-3,7-bis(dimethylamino)phenothiazine.

4. A method for stabilizing a leuco chromogen, comprising the steps of allowing the leuco chromogen to coexist in an aqueous solution comprising a compound having at least one substituent selected from the group consisting of a nitroso group and an azo group and having an ability to coordinate a metal ion or a salt thereof, wherein
the compound having at least one substituent selected from the group consisting of a nitroso group and an azo group and having an ability to coordinate a metal ion, or the salt thereof is a compound represented by the following general formula (I) or a salt thereof:

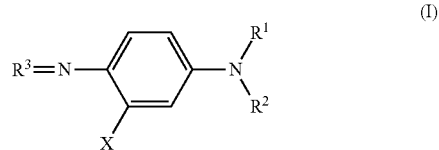

(wherein $R^1$ and $R^2$ are the same or different and each represent a hydrogen atom or a substituted or unsubstituted alkyl group; $R^3$ represents an oxygen atom or a group represented by $R^4$—N (in which $R^4$ represents a substituted or unsubstituted 2-pyridyl) and X represents a hydroxy group or an amino group).

5. The method according to claim 4, wherein the leuco chromogen is a phenothiazine chromogen.

6. The method according to claim 5, wherein the phenothiazine chromogen is 10-(carboxymethylaminocarbonyl)-3,7-bis(dimethylamino)phenothiazine.

* * * * *

UNITED STATES PATENT AND TRADEMARK OFFICE
CERTIFICATE OF CORRECTION

PATENT NO. : 9,176,066 B2  
APPLICATION NO. : 13/991655  
DATED : November 3, 2015  
INVENTOR(S) : Haruyo Soya Page 1 of 1

It is certified that error appears in the above-identified patent and that said Letters Patent is hereby corrected as shown below:

COLUMN 2:

Line 58, "sent" should read --sents--.

COLUMN 3:

Line 22, "sent" should read --sents--.

COLUMN 4:

Line 20, "sent" should read --sents--.

COLUMN 5:

Line 53, "3aminopropanesulfonic" should read --3-aminopropanesulfonic--.

COLUMN 8:

Line 38, "Of" should read --of--.

COLUMN 10:

Line 18, "stability of DA-67 against light" should read --Stability of DA-67 Against Light--.

COLUMN 12:

Line 13, "represent" should read --represents--; and  
   Line 43, "represent" should read --represents--.

Signed and Sealed this  
Twelfth Day of July, 2016

Michelle K. Lee  
*Director of the United States Patent and Trademark Office*